United States Patent [19]

Kim et al.

[11] 4,272,328
[45] Jun. 9, 1981

[54] BUFFER OVERCOAT FOR $CO_2$ ION-SELECTIVE ELECTRODES

[75] Inventors: Sang H. Kim, Rochester, N.Y.; Hao-jan Chang, Santa Clara, Calif.

[73] Assignee: Eastman Kodak Company, Rochester, N.Y.

[21] Appl. No.: 100,588

[22] Filed: Dec. 5, 1979

[51] Int. Cl.$^3$ .................... G01N 27/46; B01D 1/36
[52] U.S. Cl. .................... 204/1 T; 204/195 M; 427/58; 427/123; 427/402; 427/404; 427/419.1
[58] Field of Search ............ 204/1 T, 1 K, 195 R, 204/195 M; 427/123, 58, 402, 404, 419.1

[56] References Cited

U.S. PATENT DOCUMENTS

| | | | |
|---|---|---|---|
| 3,856,649 | 12/1974 | Genshaw et al. | 204/195 M |
| 3,896,008 | 7/1975 | Keyes | 204/195 M |
| 3,896,020 | 7/1975 | LeBlanc | 204/195 M |
| 4,053,381 | 10/1977 | Hamblen et al. | 204/195 R |
| 4,131,428 | 12/1978 | Diggens | 204/1 T |
| 4,184,936 | 1/1980 | Paul et al. | 204/195 R |

OTHER PUBLICATIONS

Tietz, "Fundamentals of Clinical Chemistry", 2nd ed., (1976), p. 893.
"Analytical Chemistry", vol. 43, No. 13, Nov. 1971, pp. 1905 & 1906.
"Analytical Chemistry", vol. 44, No. 4, Apr. 1972, pp. 856 & 857.

*Primary Examiner*—T. Tung
*Attorney, Agent, or Firm*—J. Jeffrey Hawley

[57] ABSTRACT

An ion-selective electrode for analyzing $CO_2$ concentration in a liquid sample comprises a support having thereon a metal zone, a metal halide zone, an electrolyte zone, a zone comprising a membrane comprising an ionophore and a zone comprising a hydrophilic binder and a buffer in an amount sufficient to provide a solution having a pH in the range of about 7.5 to 9.5 when wetted with about 5 $\mu$l of liquid.

18 Claims, 1 Drawing Figure

BUFFER OVERCOAT FOR CO₂ ION-SELECTIVE ELECTRODES

This application relates to a process for preparing ion-selective electrodes and the ion-selective electrodes prepared thereby. The ion-selective electrodes are useful in determining the concentration of $CO_2$ in liquids.

Control of the acid-base balance in the human body is maintained by intricate renal and pulmonary mechanisms. A disturbance in the acid-base balance is generally accompanied by changes in the electrolyte composition of the blood. Therefore, several analyses are necessary to ascertain the acid-base status. One important analysis performed in the clinical laboratory is the determination of the concentration of carbon dioxide in the blood.

Carbon dioxide dissolved in blood is in equilibrium between the interior of red blood cells and the plasma and also within the plasma. It undergoes the following reaction:

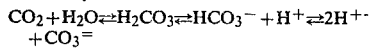

$$CO_2 + H_2O \rightleftharpoons H_2CO_3 \rightleftharpoons HCO_3^- + H^+ \rightleftharpoons 2H^+ + CO_3^=$$

The interrelationship between total $CO_2$, $HCO_3^-$, dissolved $CO_2$ and pH (not taking into account the insignificant amounts of $CO_3^=$ and carbamino compounds) is described in the literature (see *Fundamentals of Clinical Chemistry*, Norbert W. Tietz, ed., second edition, W.B. Saunders, Co., Philadelphia, Pennsylvania, p. 893, 1976). With the aid of the Henderson-Hasselbalch equation described in the literature, one can calculate pH, $pCO_2$, total $CO_2$ and $HCO_3^-$ knowing any two of these. $pCO_2$ is the partial pressure of $CO_2$ gas in a hypothetical gas phase with which the blood would be in equilibrium.

Potentiometric determination of the total $CO_2$ has been performed using a carbonate ion-selective electrode. This requires the measurement of the pH of the sample to be tested or the fixing of the pH of the sample by the addition of a buffered solution prior to testing, such as described in U.S. Pat. No. 4,131,428. This procedure, however, requires a separate step in addition to the measurement by the ion-selective electrode. Moreover, the measurement of $CO_2$ by ion-selective electrodes is further adversely affected by interferences such as gentisate, salicylate and p-aminosalicylate. Therefore, an ion-selective electrode for the determination of $CO_2$ in a liquid sample which does not require an additional step and which has a minimum of interference from gentisate, salicylate and p-aminosalicylate has been sought in the art.

DESCRIPTION OF THE DRAWING

The drawing shows a cross-sectional view of one type of an ion-selective electrode as described herein.

SUMMARY OF THE INVENTION

Figure 1:
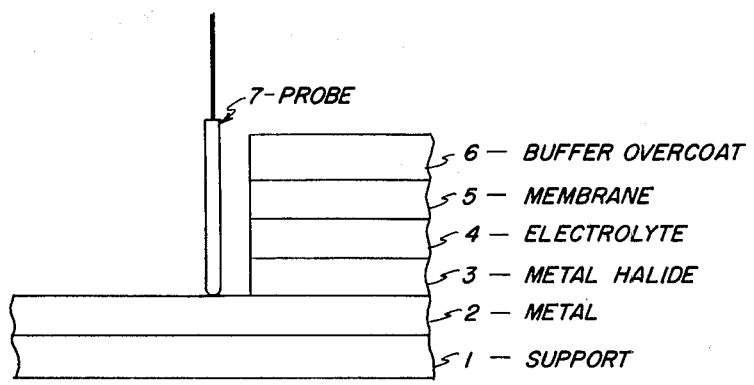

According to the present invention, there is provided an ion-selective electrode for the determination of $CO_2$ in a liquid sample comprising a support, having thereon sequentially, a metal conductive zone, a metal halide zone, an electrolyte zone and a membrane zone containing an ionophore, the improvement wherein the membrane zone is positioned between said electrolyte zone and an adjacent zone comprising a hydrophilic binder and a buffer in an amount sufficient to provide a solution having a pH in the range of about 7.5 to 9.5 when wetted with 5 μl of liquid.

It has been found that this structure not only eliminates the need to pre-buffer the sample prior to testing, but it greatly reduces the interference from gentisate, salicylate, p-aminosalicylate and other materials.

According to a further embodiment of the present invention, a process for preparing ion-selective electrodes useful for the analysis of total $CO_2$ in a liquid sample comprises coating a support having thereon successively zones of metal, metal halide, electrolyte and membrane, the improvement wherein said membrane zone is positioned between said electrolyte zone and a zone comprising a hydrophilic binder and a buffer in an amount sufficient to provide a solution having a pH in the range of from about 7.5 to 9.5 when wetted with 5 μl of liquid.

DESCRIPTION OF THE PREFERRED EMBODIMENTS

The ion-selective electrodes of the present invention comprise a support having thereon, successively, a metal zone, a metal halide zone, a zone containing a metal salt electrolyte, a membrane zone comprising an ionophore and a buffer zone comprising a hydrophilic binder and a buffer in an amount sufficient to provide a solution having a pH in the range of from about 7.5 to about 9.5 when wetted with about 5 μl amount of liquid (preferably water or liquid sample to be tested).

The zones can be either in the form of a layer containing first a metal zone, then successively a metal halide zone, a zone containing an electrolyte, a membrane zone and then the buffer zone wherein the material to be assayed, with or without a carrier material, is first introduced to the buffer zone, or preferably they are in the form of separate layers successively coated over the support.

Suitable supports for the metal layer are preferably insulating and include glass, paper and polymeric supports such as polyesters such as poly(ethylene terephthalate), cellulose esters and the like.

The metal zone can comprise any conducting metal such as silver, nickel, gold, platinum and the like. The preferred metal layer comprises silver.

The metal layer or metal zone can be formed in situ or coated onto the support using any suitable method of depositing a thin metal layer. Thus, the metal layer can be formed by electroless deposition, vacuum-depositing metal, depositing a photographic layer such as silver halide and exposing and developing to form silver and the like.

The metal halide zone or layer, which along with the metal zone or layer forms the reference electrode, comprises a metal salt wherein the metal portion is identical to the metal layer and the halide can be chloride, bromide and the like. In the preferred embodiment, the metal layer is silver and the metal halide layer is silver chloride.

The metal halide zone or layer can be formed either adjacent to or over the metal layer using a variety of well known techniques. The metal layer can be treated with an oxidizing agent such as $KClCrO_3$, $K_3Fe(CN)_6$, $KMnO_4$, $K_2Cr_2O_7$, $NH_4VO_3$ and the like or combinations thereof to oxidize the surface of the metal layer or the metal layer can be coated with a metal halide emulsion and dried. A common technique for coating the metal halide layer comprises plating. The coverage of the metal layer can preferably be from 0.1 to 10 g/m² and the metal halide layer can preferably be from 0.1 to 2 g/m².

The layers of metal and metal halide comprise the reference electrode layers. Coated adjacent to or on the metal halide layer is the electrolyte layer or zone. The electrolyte zone comprises a hydrophilic binder and a metal salt. Typically, the binder and salt are in solution with a solvent for both.

The binder for the electrolyte zone or layer may comprise any hydrophilic material suitable for the formation of continuous, coherent, cohesive layers compatible with the salt of the electrolyte layer. If formed by coating, the electrolyte layer may be applied in a solvent for both the ionic salt and the polymeric binder. Preferred binder materials of this type are hydrophilic, natural and synthetic polymeric film-forming materials, such as polyvinyl alcohol, gelatin, agarose, deionized gelatin, polyacrylamide, polyvinyl pyrrolidone, polyhydroxyethyl acrylate, polyhydroxyethyl methacrylate, polyacrylic acid, etc. Specifically preferred from among these materials are the hydrophilic colloids, such as gelatin (especially deionized gelatin), agarose, polyvinyl alcohol and polyhydroxyethyl acrylate.

The metal salt, which is preferably dissolved in the binder, will be determined by the ion to be determined. For example, in the $CO_2$(carbonate)-selective electrode, which preferably uses AgCl as the metal halide, alkali chloride and alkali carbonate are logical choices, although alkali bicarbonates may also be used. Since the carbonate-selective membrane is sensitive to chloride ion, the alkali chloride may be sufficient in the electrolyte zone. The salt will generally be a water-soluble salt having a cation selected from ammonium, alkali metals and alkaline earth metals, mixtures of the same or any other suitable salt to which the electrode responds. The anion can be a halogen or sulfur-containing material, depending upon the composition of the metal-salt layer. In addition, anion sensitive to the $CO_2$-selective membrane may be added to poise the inner membrane surface. In the case of a $CO_2$-selective electrode, $Cl^-$ alone without $CO_3^=/HCO_3^-$ was sufficient. Conductive metal salts of these anions are commonly insoluble in water.

Appropriate coating solvents for the polymeric binder and ionic salt will depend largely on the nature of the polymer and the salt. Generally, polar solvents suitable for dissolving the salt and the polymer are satisfactory. Thus, water is a preferred solvent for layers of hydrophilic materials, such as polyvinyl alcohol and gelatin.

The electrolyte layer can contain other addenda such as surfactants such as octylphenoxy polyethoxy ethanol (Triton X-100 by Rohm and Haas Company), p-isononylphenoxy polyglycidol (Surfactnat 10G by Olin Corporation), polyethylene glycol ether of linear alcohols (Tergitol 15-S-7 by Union Carbide Corporation) and a nonionic fluorosurfactant (Zonyl FSN by Dupont Corporation). Other addenda include adhesives to improve the adhesion to the membrane layer. Useful adhesives include Adhesive 72-1153 (by National Starch Company), acrylates such as poly(n-butyl acrylate) and poly(n-butyl acrylate-co-2-acrylamido-2-methylpropane sulfonic acid)sodium salt, (weight ratio 95:5) and the like.

The electrolyte layer can be of any thickness but preferred electrolyte layers comprise binders in concentration of 1 to 20 g/m², metal salt in concentration of 0.1 to 15 g/m², surfactants in concentration of 0 to 1 g/m² and adhesives in concentration of 0 to 2 g/m².

The particular drying conditions which must be applied to the reference electrode in the manufacture of any specific ion-selective electrode will, of course, vary greatly, depending upon the composition of the electrode layers, particularly the binder(s) used, the solvent(s) or dispersing medium(s) used to form the layer, and these can be readily determined by the skilled artisan. Typical such conditions are described in the examples below for layers of the composition described therein.

The membrane zone or layer can be any membrane zone or layer known in the art and comprises a binder and an ionophore (or ion carrier). The membrane can be coated adjacent to or over the reference and electrolyte layers by any means such as roll coating, dip coating and the like.

The following patents and publications describe ion-selective membranes of the type described in the instant invention:

U.S. Pat. No. 3,562,129 to Simon, issued Feb. 9, 1971;
U.S. Pat. No. 3,753,887 to Kedem et al, issued Aug. 21, 1973;
U.S. Pat. No. 3,856,649 to Genshaw et al, issued Dec. 24, 1974;
British Pat. No. 1,375,446, issued Nov. 27, 1974;
German OLS No. 2,251,287, issued Apr. 26, 1973;
W. E. Morf, D. Ammann, E. Pretsch and W. Simon, "Carrier Antibiotics and Model Compounds as Components of Ion-Sensitive Electrodes, *Pure and Applied Chemistry*, Volume 36, No. 4, pages 421 through 439 (1973);
R. W. Cattrall and H. Freiser, *Analytical Chemistry*, 43, 1905 (1971);
H. James, G. Carmack and H. Freiser, *Analytical Chemistry*, 44, 856 (1972);
U.S. Pat. No. 3,723,281 to Wise, issued Mar. 1973;
H. B. Herman and G. A. Rechnitz, "Science," 184, 1074 (1974), *Analytical Letter*, 8, 147 (1975), *Analytical Chimica Acta*, 76, 155 (1975); and
G. A. Rechnitz, G. J. Nogle, M. R. Bellinger and H. Lees, *Clinical Chimica Acta*, 76, 295 (1977).

The membrane layer generally contains binders, ion carriers, solvents and the like, such as described in copending U.S. Application Ser. No. 893,656, filed Apr. 5, 1978.

Membranes of this type are well known. Such membranes generally include an inert hydrophobic binder or matrix having dispersed therein an ion carrier or selector commonly referred to as an ionophore which imparts selectivity to the membrane. These membranes can also contain a carrier solvent for the ionophore to provide adequate ion mobility in the membrane. The carrier solvent generally also serves as a plasticizer for the membrane binder.

Particular binders useful in the membranes described herein include, among others, poly(vinyl chloride), carboxylated poly(vinyl chloride), poly(vinyl chloride-co-vinyl acetate), poly(vinyl chloride-co-vinyl acetate-co-vinyl alcohol), copolymers of vinylidene chloride/acrylonitrile, poly(styrene-co-acrylonitrile) and combinations of the above.

Useful ionophores include 4'-alkyl-$\alpha\alpha\alpha$-trifluoroacetophenone (or trifluoroacetyl-p-alkyl benzene) having the general structure:

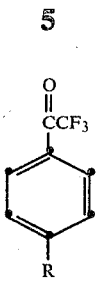

where R is $n-C_4H_7$, $n-C_6H_{13}$, $n-C_8H_{17}$, $n-C_{10}H_{21}$ and $n-C_{12}H_{25}$. Other ionophores selective for $CO_2$ may also be used.

The membrane zone or layer can also contain carrier solvents such as phthalates such as diisodecyl phthalate, bis(2-ethylhexyl) phthalate, dioctyl phthalate, dinonyl phthalate, diundecyl phthalate, didecyl phthalate, didodecyl phthalate and the like; sebacates such as bis(2-ethylhexyl)sebacate, trimellitates such as triisodecyl trimellitate and tris(2-ethylhexyl) trimellitate; phosphates such as tris(2-ethylhexyl) phosphate; glycolates; adipates such as diisodecyl adipate; glutarates such as diisodecylglutarate; polymeric plasticizers and the like.

The membrane layer can also contain ion exchangers, which are materials capable of selectively associating or exchanging with desired anion or carbonate ions, such as quaternary ammonium salts such as trioctylpropylammonium chloride, trioctylpropylammonium bromide, trioctylpropylammonium iodide, tridodecylmethylammonium p-toluenesulfonate, 3,4-dichlorobenzyldimethyloctadecylammonium chloride, tricaprylmethylammonium chloride, didodecyldimethylammonium chloride, poly(styrene-co-vinylbenzyltrihexylammonium chloride) and the like.

Other addenda useful in the membrane layer include surfactants, such as poly(dioctyl-co-methylphenyl siloxane), Triton X-100, Tergitol 15-S-7, Zonyl FSN, Surfactant 10G, Span 80 (by Atlas Chemical Company), FC-134 (by 3M Company) and the like.

The membrane zone or layer can be coated using various coating solvents such as 2-butanone, tetrahydrofuran and others described in *Research Disclosure* 16113, published by Industrial Opportunities Limited, Homewell Havant, Hampshire P09 1EF, U.K., Volume 161, September 1977.

The membrane zone or layer preferably comprises binders in concentration of 1 to 30 g/m², ion carrier in concentration of 0.1 to 45 g/m², carrier solvent in concentration of 0 to 45 g/m², ion exchangers in concentration of 0.1 to 10 g/m² and surfactants in concentration of 0 to 1 g/m².

The buffer zone or layer comprises a hydrophilic binder and a buffer in an amount sufficient to provide a solution having a pH in the range of about 7.5 to 9.5 when wetted with 5 μl of liquid.

The hydrophilic binders useful herein include agarose, gelatin, poly(vinyl alcohol) and synthetic vinyl polymers comprising:

(a) 75 to 100 weight percent of polymerized hydrophilic monomers selected from:
  (1) 0 to 100, preferably 80 to 100, weight percent N-vinylpyrrolidone;
  (2) 0 to 90, preferably 15 to 90, weight percent acrylamide;
  (3) 0 to 75 weight percent N-isopropylacrylamide;
  (4) 0 to 50, preferably 15 to 45, weight percent of an acrylic acid, preferably acrylic acid or methacrylic acid;
  (5) 0 to 60, preferably 10 to 50, weight percent of a hydroxyalkyl acrylate, preferably hydroxyethyl acrylate or hydroxyethyl methacrylate;
  (6) 0 to 70, preferably 15 to 65, weight percent of a sulfoalkyl acrylate or an N-(sulfoalkyl)-acrylamide, including the alkali metal and ammonium salts thereof, such as described in U.S. Patents 2,923,734, 3,024,221, 3,411,911, 3,506,707 and 3,547,899, preferably 2-acrylamido-2-methylpropanesulfonic acid; and (b) 0 to 25, preferably 1 to 20, weight percent of an active methylene group-containing monomer such as those described in U.S. Pat. Nos. 3,459,790, 3,929,482 and 3,939,130, preferably 2-acetoacetoxyethyl methacrylate.

Specific examples include:
(a) agarose;
(b) deionized gelatin;
(c) gelatin hardened with bis(vinylsulfonylmethyl) ether;
(d) poly(vinyl alcohol);
(e) poly(vinyl pyrrolidone);
(f) poly(acrylamide-co-N-vinyl-2-pyrrolidone-co-2-acetoacetoxyethyl methacrylate) (19:80:1);
(g) poly(acrylamide-co-2-acetoacetoxyethyl methacrylate) (90:10);
(h) poly(2-hydroxyethyl methacrylate-co-2-acrylamido-2-methylpropanesulfonic acid, sodium salt) (38:62);
(i) poly(2-hydroxyethyl methacrylate-co-2-acrylamido-2-methylpropanesulfonic acid, sodium salt-co-2-acetoacetoxyethyl methacrylate) (35:55:10);
(j) polymer (i) having ratio of 35:45:20;
(k) poly(2-hydroxyethyl methacrylate-co-methacrylic acid, sodium salt-co-2-acetoacetoxyethyl methacrylate) (50:42:8);
(l) poly(N-isopropylacrylamide-co-2-acrylamide-2-methylpropanesulfonic acid, sodium salt-co-2-acetoacetoxyethyl methacrylate) (9:82:9);
(m) poly(N-isopropylacrylamide-co-2-acrylamide-2-methylpropanesulfonic acid, sodium salt-co-2-hydroxyethyl acrylate) (43:31:26);
(n) polymer (m) having ratio of 74:16:10;
(o) poly(2-hydroxyethyl acrylate-co-methacrylic acid, sodium salt-co-N-isopropylacrylamide) (37:27:36);
(p) polymer (o) having a ratio of 47:18:35;
(q) poly(2-hydroxyethyl acrylate-co-acrylic acid, sodium salt-co-N-isopropylacrylamide) (36:23:41; equimolar ratio);
(r) poly(2-hydroxyethyl acrylate-co-2-hydroxyethyl methacrylate-co-2-acrylamido-2-methylpropanesulfonic acid, sodium salt) (25:29:46);
(s) poly(2-hydroxyethyl methacrylate-co-methacrylic acid, sodium salt-co-methacrylamide-co-2-acetoacetoxyethyl methacrylate) (28:34:28:10); and
(t) poly(2-hydroxyethyl acrylate-co-2-acrylamido-2-methylpropanesulfonic acid, sodium salt) (53:47).

The buffer, which produces solutions having a pH range, preferably of 8 to 9, can comprise any buffer salt conventionally used, preferably those having acid dissociation constants (pKa), between 8 to 9. Preferred bases include tris(hydroxymethyl)aminomethane, diethanolamine, 2-amino-2-methyl-1,3-propanediol and 2-amino- 2-ethyl-1,3-propanediol and the like in combination with acidic components such as HX, wherein X is an anion which does not significantly interfere with the response to $CO_3^=$ such as $Cl^-$, $Br^-$, $F^-$ and $I^-$ or polymeric sulfonic and acrylic acids. Also particularly useful are acids such as N,N-bis(2-hydroxyethyl)glycine, tris(hydroxymethyl)methylaminopropanesulfonic acid and the like in combination with alkalis such as LiOH and NaOH. Buffer salts useful herein can be selected from those described in "Data for Biochemical Research" by R. M. C. Dawson et al, $2^{nd}$ Ed., Oxford University Press, 1969.

The buffer must be present in an amount sufficient to provide a solution having a pH in the range of about 7.5 to 9.5 when wetted with about 5 µl amount of liquid. A preferred concentration of buffer which achieves this result is from 5 to 480 mM/m².

The buffer layer can also include addenda such as surfactants including any of those described earlier. The buffer layer can be applied over the membrane layer of the electrode by any conventional technique such as lamination, coating or otherwise depositing the layers one over the other. For barrel-type electrodes, dipping or other methods may be used. Drop coating or extrusion techniques may be used, or a material such as filter paper imbibed with the buffer solution may be applied in planar electrodes.

The buffer layer preferably comprises hydrophilic binders in concentration of 1 to 20 g/m², buffer salts in concentration of 5 to 480 mM/m², surfactants in concentration of 0 to 1 g/m² and plasticizers in concentration of 0 to 3 g/m².

A typical manufacturing process for an ion-selective electrode according to the present invention, as depicted in the drawing, would include applying the metal (preferably silver) layer 2 onto a support 1 [preferably poly(ethylene terephthalate)], drying, overcoating the metal layer with a metal halide layer 3, by treating the metal surface with an oxidizing agent and drying. The electrolyte layer 4 is applied by solution coating and drying and overcoating with a membrane layer 5, which is dried and overcoated with the buffer layer 6. A potential is set up using the probe 7 connected to metal layer 2.

In some instances it is desirable to coat layers 3 to 6, and in some instances just layer 2, in a striped fashion so that the metal layer is exposed in some areas. In this way the probe can be contacted easily with the metal layer.

The various layer thicknesses can be varied over a wide range. Various preferred layer thicknesses are 2 to 20 mils for layer 1, 0.1 to 2µ for layer 2, 0.01 to 0.2µ for layer 3, 0.5 to 20µ for layer 4, 1 to 30µ for layer 5 and 1 to 30µ for layer 6.

In a further preferred embodiment, a hydrophobic overcoat can be applied to the buffer overcoat to increase the buffer capacity of the buffer layer and reduce the hydrophilicity of the buffer layer surface. Useful overcoats comprise cellulose esters with polyol humectants which can be coated from solvents.

The optional overcoat can generally comprise from 0 to 5 g/m² concentration of binder with 0 to 1 g/m² of humectant and 0 to 1 g/m² of surfactants.

The ion selectivity of membrane electrodes, such as the electrodes of the present invention, can be observed by measuring a steady-state difference in electrical potential between reference solutions and sample solutions, as described in the above-identified U.S. Application Ser. No. 893,656.

In one preferred embodiment, the $CO_2$ ion-selective electrode has the following structure:

| | | | Range |
|---|---|---|---|
| Buffer Layer | Binder: | poly(2-hydroxyethyl acrylate-co-sodium acrylate-co-N-isopropylacrylamide) (36:23:41 by weight) | 2.5–20 g/m² |
| | Buffer Salt: | tris(hydroxymethyl)aminomethane . hydrogen fluoride (tris . HF) and | 15–120 mM/m² |
| | | tris(hydroxymethyl)aminomethane (tris) | 15–120 mM/m² |
| | Surfactant: | Surfactant 10G | 0.01–1.0 g/m² |
| Membrane Layer | Binder: | *Vinylite (VYNS) and *Vinylite (VAGH) (60:40 by weight) | 5–20 g/m² |
| | Ion Carrier: | decyltrifluoroacetophenone | 1–15 g/m² |
| | Carrier Solvent: | Diisodecyl phthalate | 1–15 g/m² |
| | Ion Exchanger: | trioctylpropylammonium chloride | 0.1–10 g/m² |
| | Surfactant: | Dow Corning fluid 510 | 0.01–1 g/m² |
| Electrolyte Layer | Binder: | deionized gelatin | 1–10 g/m² |
| | Metal Salt: | combination of NaCl and KCl (3:1 by weight) | 1–5 g/m² |
| | Surfactant: | Triton X-100 | 0.01–1 g/m² |
| Metal Halide Layer | | AgCl | 0.1–2 g/m² |
| Metal Layer | | Ag° support | 0.5–10 g/m² |

*VAGH = poly(vinyl chloride-co-vinyl acetate-co-vinyl alcohol) (91:3:6)
*VYNS = poly(co-vinyl acetate-co-vinyl alcohol) (90:10)

The following examples will serve to better demonstrate the successful practice of the present invention.

EXAMPLE 1

$CO_2$ ion-selective electrodes were prepared according to the preferred embodiment described immediately above. The control electrode had no buffer layer and the electrode of Example 1 had a buffer layer comprising:

| | | |
|---|---|---|
| Binder: | poly(2-hydroxyethyl methacrylate-co-sodium-2-acrylamido-2-methylpropane-sulfonate-co-acetoacetoxyethyl methacrylate) (35:55:10) | 2.5 g/m² |
| Buffer: | Tris(hydroxymethyl)aminomethane | 30.0 mM/M² |
| | Tris(hydroxymethyl)aminomethane . HF | 30.0 mM/m² |
| Surfactant: | Surfactant 10G | 0.1 g/m² |

The electrodes were tested by spotting 10 µl aliquots of each of three dialyzed human serum $CO_2$ calibrators having concentrations and pH described in Table I below, and the potentials (mV) were measured as a function of time (3 minutes) against a microreference electrode (MI-401). The microreference electrode (MI-401) is a silver/silver chloride internal reference electrode manufactured by Microelectrodes, Inc., Londonderry, N.H. 03053. The sample drop was confined in a hole of 0.08 cm² electrode area. Results shown in Table I indicate that the buffered overcoat provides a slope much nearer to the ideal (−29 mV/dec).

TABLE I

| Calibrator Level | 2 | 3 | 5 | Slope mV/dec |
|---|---|---|---|---|
| $CO_2$, mM | 8.9 | 19.2 | 45.5 | |
| pH | 7.30 | 7.41 | 7.80 | |
| (A) Control | 25.0 (mV) | 24.1 (mV) | 21.9 (mV) | −6 |
| | 26.5 (mV) | 22.0 (mV) | 20.5 (mV) | |
| (B) Test | 31.1 (mV) | 21.3 (mV) | 11.6 (mV) | |
| | | | | −25 |
| Electrode | 28.5 (mV) | 20.8 (mV) | 12.6 (mV) | |

EXAMPLE 2

Several electrodes were prepared with buffer layers as described above except that the binders used and thickness of the buffer layers were varied, as shown in Table II. The electrodes were tested as above using $CO_2$ values obtained from a Corning 165/2 pH blood gas analyzer as reference. Results shown in Table II indicate that several binders produce acceptable results compared to unbuffered electrodes.

TABLE II

| Example | Polymer/Thickness* | Slope mV/dec | Average Bias** mM | % |
|---|---|---|---|---|
| 2A | (i) 1X | −24.0 ± 2.7 | +2.7 | 13 |
| 2B | (i) (½)X | −24.2 ± 1.4 | −3.4 | 16 |
| 2C | (o) (½)X | −31.1 ± 2.6 | 0 | 0 |
| 2D | (o) 1X | −29.5 ± 2.3 | +2.9 | 13 |
| 2E | (m) 1X | −19.5 ± 0.6 | −5.3 | −25 |
| 2F | (h) 1X | −19.8 ± 1.0 | −0.7 | −3 |
| control | none | | −6 | |

*1X thickness = 5 g/m² polymer, 60 mM/m² tris(hydroxyethyl)aminomethane, 60 mM/m² tris(hydroxyethyl)aminomethane . HF, 0.1 g/m² 10G.
**Average bias is the difference in measured concentration between the electrode and the reference. Control pool contains 21.5 mM$CO_2$.

EXAMPLE 3:

$CO_2$ Determinations Using a pH-Controlling Overcoated Electrode (Dynamic Range 8–60 mM)

Electrodes were prepared as in Example 2 using in the buffer layer:

| | | |
|---|---|---|
| Binder: | Poly(2-hydroxyethyl acrylate-co-acrylic acid, sodium salt-co-N-isopropylacrylamide (36:23:41 equimolar ratio) | 5.0 g/m² |
| Buffer: | Tris(hydroxymethyl)aminomethane | 60.0 mM/m² |
| | Tris(hydroxymethyl)aminomethane . HF | 60.0 mM/m² |
| Surfactant: | Surfactant 10G | 0.1 g/m² |

The electrodes were tested as above using 7-level human serum based calibrator solutions. Assay values obtained from a Beckman Cl/$CO_2$ analyzer were used as reference. A slope of −22.75 mV/decade $CO_2$ concentration over the 8–60 mM dynamic range was obtained.

EXAMPLE 4

A buffered electrode was prepared as in Example 3 using in the buffer layer:

| | | |
|---|---|---|
| Binder: | Deionized gelatin type V | 7.5 g/m² |
| Buffer: | 2-amino-2-methyl-1,3-propanediol (BHAM) 2-amino-2-methyl-1,3-propanediol-hydrogen fluoride | 22.5 mM/m² 22.5 mM/m² |
| Surfactant: | Tergitol 15-S-7 | 0.08 g/m² |

The electrode was tested by spotting 50 μl aliquots of $NaHCO_3$ solutions of varying concentrations (3, 10, 30, 100 mM). Duplicate potentials were measured against a MI-401 microreference electrode. The 3-minute potentials, tabulated in Table III, gave a slope of −20 mV/decade $HCO_3^-$ concentration.

TABLE III

| $HCO_3^-$ Concentration mM | Potentials mV | |
|---|---|---|
| 3 | 17.2 | |
| 10 | 7.6, | 6.6 |
| 30 | −0.1, | −3.1 |
| 100 | −12.1, | −13.9 |

EXAMPLE 5

Coatings of Example 3 were duplicated both with and without (control) a buffer layer. The ΔmV bias due to interference from salicylate and probenecid (4-[(dipropylamino)sulfonyl]benzoic acid) were measured and compared as shown in Table IV.

Table IV

| Interferent | Spiked Level* mg/dl | ΔmV Bias Control | ΔmV Bias Example 5 |
|---|---|---|---|
| Salicylate | 24 | −42 | −5.0 |
| Probenecid | 14 | −9.5 | +0.7 |

*in control pool

EXAMPLE 6

Reduction of Interferences from Gentisic Acid and p-Aminosalicylic Acid in $CO_2$ Electrodes Gentisate, a metabolite of aspirin, and p-aminosalicylate, an antituberculin drug, are known to interfere with $CO_2$ electrodes. Accordingly, two electrodes were prepared according to the format and methods described in Example 3. Electrode No. 1 (bare) was used as the control; electrode No. 2 was prepared in a similar manner except that it contained a buffer overcoat comprised of 60 mM/m² of tris(hydroxymethyl)aminomethane, 60 mM/M² of tris(hydroxymethyl)aminomethane hydrogen fluoride, 12.0 g/m² of poly(2-hydroxyethyl acrylate-co-acrylic acid, sodium salt-co-N-isopropyl-acrylamide) (36:23:41 by weight), and 0.12 g/m² Surfactant 10 G.

The electrodes were tested during a microreference electrode and 10 μl drops of solutions containing 0.02 M $KHCO_3$ and 0.1 M NaCl with varying amounts of sodium gentisate in one case and varying amounts of p-aminosalicylate in another. Results, shown in the table below, illustrate the effectiveness of the buffer overcoat in reducing the interference.

TABLE IV

| Electrode | Sodium Gentisate Concentration mM | mV | ΔmV | % Reduction |
|---|---|---|---|---|
| No. 1 (Control) | 0 | 5.9 | | |
| | 0.3 | 0.6 | −5.3 | 0 |
| | 1.0 | −4.0 | −9.9 | 0 |
| | 3.0 | −16.6 | −22.5 | 0 |
| | 10.0 | −40.5 | −46.4 | 0 |

TABLE IV-continued

| | | | | |
|---|---|---|---|---|
| No. 2 (Buffer) | 0 | 24.7 | | |
| | 0.3 | 23.3 | −1.4 | 74 |
| | 1.0 | 17.8 | −6.9 | 30 |
| | 3.0 | 7.5 | −17.2 | 24 |
| | 10.0 | −18.0 | −42.7 | 8 |
| Sodium p-Amino-salicylate Concentration mM | | | | |
| No. 1 (Control) | 0 | 5.9 | | |
| | 0.3 | −0.6 | −6.5 | 0 |
| | 1.0 | 6.9 | −10.2 | 0 |
| | 3.0 | −2.1 | −17.0 | 0 |
| | 10.0 | −32.7 | −38.6 | 0 |
| No. 2 (Buffer) | 0 | 24.7 | | |
| | 0.3 | 21.1 | −3.6 | 45 |
| | 1.0 | 21.8 | −2.9 | 72 |
| | 3.0 | 12.3 | −12.4 | 27 |
| | 10.0 | −9.4 | −34.1 | 12 |

The invention has been described in detail with particular reference to preferred embodiments thereof, but it will be understood that variations and modifications can be effected within the spirit and scope of the invention.

It is claimed:

1. In an ion-selective electrode for analyzing $CO_2$ concentration in a liquid comprising a support having thereon a layer or layers having sequentially metal/metal halide reference electrode zones, an electrolyte zone and a membrane zone containing an ionophore, the improvement wherein said membrane zone is positioned between said electrolyte zone and an adjacent zone comprising a hydrophilic binder and a buffer in an amount sufficient to provide a solution having a pH in the range of 7.5 to 9.5 when wetted with about 5 µl of liquid to be analyzed.

2. The ion-selective electrode of claim 1 wherein all of the zones are in one layer on the support.

3. The ion-selective electrode of claim 1 wherein each zone is a separate layer.

4. The ion-selective electrode of claim 3 wherein the metal/metal halide reference electrode layers are silver and silver halide layers, respectively.

5. The ion-selective electrode of claim 3 wherein the ionophore is 4'-alkyl-$\alpha\alpha\alpha$-trifluoroacetophenone.

6. The ion-selective electrode of claim 1 wherein the buffer is present in an amount sufficient to provide a solution having a pH in the range of 7.5 to 9.5 when wetted with about 5 µl of serum.

7. The ion-selective electrode of claim 3 wherein the buffer comprises a member selected from the group consisting of tris(hydroxymethyl)aminomethane, diethanolamine, 2-amino-2-methyl-1,3-propanediol and 2-amino-2-ethyl-1,3-propanediol.

8. The ion-selective electrode of claim 3 wherein the layer containing said buffer solution also comprises a surfactant.

9. The ion-selective electrode of claim 3 wherein said hydrophilic binder is selected from the group consisting of gelatin, poly(vinyl alcohol) and poly(2-hydroxyethyl acrylate-co-sodium acrylate-co-N-isopropylacrylamide) (36:23:41 by weight).

10. In a process of preparing an ion-selective electrode for analyzing $CO_2$ concentration in a liquid comprising coating a support with, in succession, layers of metal, metal halide, electrolyte layer and a membrane layer comprising an ionophore, the improvement wherein the membrane layer is overcoated with a layer comprising a hydrophilic binder and a buffer in an amount sufficient to provide a solution having a pH in the range of from about 7.5 to 9.5 when wetted with 5 µl of liquid to be analyzed.

11. The process of claim 10 wherein the metal layer comprises silver.

12. The process of claim 10 wherein the metal halide layer is silver chloride.

13. The process of claim 10 wherein the ionophore is 4'-alkyl-$\alpha\alpha\alpha$-trifluoroacetophenone.

14. The process of claim 10 wherein the buffer comprises a member selected from the group consisting of tris(hydroxymethyl)aminomethane, diethanolamine, 2-amino-2-methyl-1,3-propanediol and 2-amino-2-ethyl-1,3-propanediol.

15. The process of claim 14 wherein the layer containing said buffer solution also comprises a surfactant.

16. The process of claim 10 wherein said hydrophilic binder is selected from the group consisting of gelatin, poly(vinyl alcohol) and poly(2-hydroxyethyl acrylate-co-sodium acrylate-co-N-isopropylacrylamide) (36:23:41 by weight).

17. The process of claim 10 wherein said buffer is present in an amount sufficient to provide a solution having a pH in the range of from about 7.5 to 9.5 when wetted with 5 µl of serum.

18. The process of assaying for $CO_2$ concentration in a liquid sample comprising contacting the sample with the buffer zone of the ion-selective electrode of claim 1.

* * * * *